United States Patent [19]

Petrosky

[11] Patent Number: 5,315,050
[45] Date of Patent: May 24, 1994

[54] MANUFACTURE OF PERCHLOROETHYLENE FROM CARBON TETRACHLORIDE IN THE PRESENCE OF HYDROGEN

[75] Inventor: Jimmie T. Petrosky, Wichita, Kans.

[73] Assignee: Vulcan Materials Company, Wichita, Kans.

[21] Appl. No.: 16,238

[22] Filed: Feb. 11, 1993

[51] Int. Cl.$^5$ .................. C07C 17/04; C07C 17/26
[52] U.S. Cl. .................................... 570/234; 570/237
[58] Field of Search ..................... 570/234, 218, 237

[56] References Cited

U.S. PATENT DOCUMENTS

| | | | |
|---|---|---|---|
| 1,930,350 | 10/1933 | Strosacker et al. | 260/166 |
| 2,442,323 | 5/1948 | Davis et al. | 260/654 |
| 2,442,324 | 5/1948 | Heitz et al. | 260/654 |
| 2,447,410 | 8/1948 | Hampel | 260/654 |
| 2,577,388 | 12/1951 | Warren | 260/654 |
| 2,727,076 | 12/1955 | Warren | 260/658 |
| 2,857,438 | 10/1958 | Obrecht et al. | 260/654 |
| 3,234,295 | 2/1966 | Sprauer | 570/218 |
| 3,364,272 | 1/1968 | Ager, Jr. | 260/654 |
| 4,002,695 | 1/1977 | Gorton et al. | 260/654 D |
| 5,023,387 | 6/1991 | West et al. | 570/252 |

*Primary Examiner*—Howard T. Mars
*Attorney, Agent, or Firm*—Burns, Doane, Swecker & Mathis

[57] ABSTRACT

Perchloroethylene and hydrogen chloride are made by thermal noncatalytic pyrolysis of carbon tetrachloride in the presence of elemental hydrogen and chlorine under conditions which maximize consumption of carbon tetrachloride while minimizing the production of heavy ends.

19 Claims, 2 Drawing Sheets

MANUFACTURE OF PERCHLOROETHYLENE FROM CARBON TETRACHLORIDE IN THE PRESENCE OF HYDROGEN

BACKGROUND OF THE INVENTION

1. Field of the Invention

This invention relates to a process for making perchloroethylene by thermal, noncatalytic pyrolysis of carbon tetrachloride in the presence of elemental hydrogen and chlorine at relatively low temperatures. In particular, it relates to a process for production of perchloroethylene and hydrogen chloride using carbon tetrachloride as both the principal reactant and a reactive diluent under conditions which maximize consumption of unwanted carbon tetrachloride, while minimizing the production of heavy ends, such as hexachlorobenzene and other tarry products.

2. Background of the Invention

When conventionally manufacturing perchloroethylene by chlorination of hydrocarbons and/or their partially chlorinated derivatives, substantial amounts of carbon tetrachloride are also obtained. In addition, substantial quantities of undesirable highly chlorinated products such as hexachloroethane, hexachlorobutadiene and hexachlorobenzene, hereinafter referred to as heavy ends, are formed. Carbon tetrachloride, however, is thought to be among the halocarbons which cause destruction of the ozone layer and is therefore coming to be considered a relatively undesirable product. It has also been used as a feedstock in producing environmentally deleterious fully halogenated chlorofluorocarbons and demand for it is therefore decreasing for this reason as well. Because of these undesirable environmental attributes of carbon tetrachloride, regulations governing the production and use of carbon tetrachloride are expected to result in a marked decrease in demand for carbon tetrachloride over the next decade. The heavy ends resulting from conventional processes for producing perchloroethylene are also undesirable and their disposal by burning can result in emission of undesirable compounds into the atmosphere. On the other hand, the ecologically more benign chlorinated hydrocarbons, notably perchloroethylene, are expected to remain in high demand because of their many practical uses, both as a solvent and as a starting material for the production of other chemicals. The present invention addresses this situation by providing a process for the production of perchloroethylene that consumes carbon tetrachloride and minimizes formation of heavy ends.

Perchloroethylene can be produced by pyrolysis of carbon tetrachloride at high temperatures as mentioned in U.S. Pat. No. 1,930,350. As explained in U.S. Pat. No. 3,364,272, the pyrolysis process for production of perchloroethylene ordinarily requires reaction temperatures of the order of 800° C. The pyrolysis of carbon tetrachloride discussed in U.S. Pat. No. 2,447,410, requires a temperature of 1300° to 1400° C. The production of perchloroethylene at these high temperatures, however, has serious disadvantages. Notably, the use of the high pyrolysis temperatures generally requires high energy input to initiate and maintain the reaction, expensive materials for reactor construction, and elaborate product separation to remove the unwanted heavy ends.

Catalytic systems have also been used to produce perchloroethylene. U.S. Pat. No. 4,002,695, for instance, discloses a process for preparing perchloroethylene by reaction of carbon tetrachloride vapor with hydrogen in the presence of a barium chloride catalyst at a temperature of at least 500° C. However, the catalysts required in this method are expensive and subject to deactivation due to fouling with carbon. The production of unwanted heavy ends, such as hexachloroethane, hexachlorobutadiene and hexachlorobenzene, is also promoted by the use of such catalyst.

Figure 1:
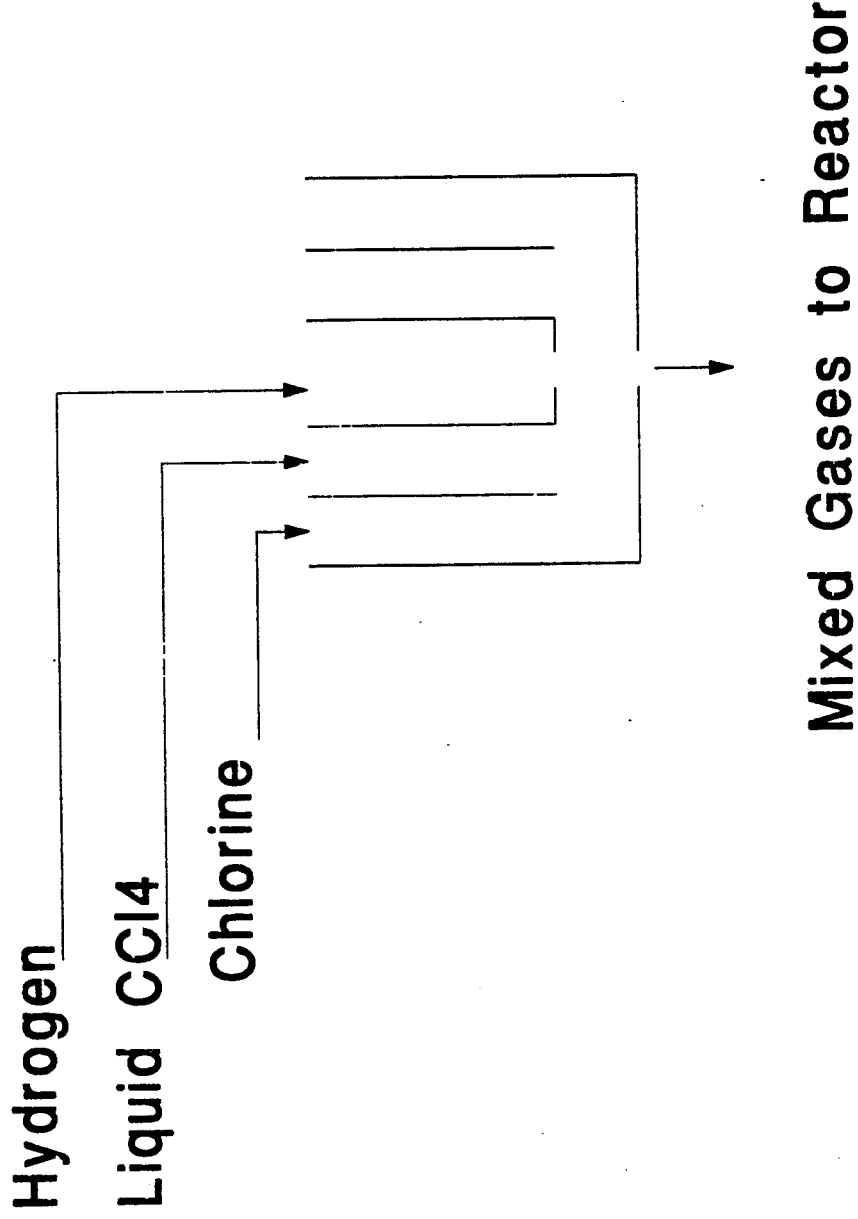
FIGS. 1 and 2 are schematic representations of two types of mixing schemes for introducing feed into the reaction zone.

In these schemes, the feed is introduced into a mixing nozzle comprising a mixing zone where the reactants are pre-mixed, the mixing nozzle is inserted through a feed port into the reaction zone of the reactor, and the feed comprising the pre-mixed reactants is discharged from the mixing nozzle into the reaction zone of the reactor.

SUMMARY OF THE INVENTION

The present invention provides a noncatalytic thermal process for making perchloroethylene and hydrogen chloride from carbon tetrachloride, elemental hydrogen and chlorine by introducing these reactants into a reaction zone, with the hydrogen and chlorine being introduced in amounts sufficient to provide heat for the pyrolysis of carbon tetrachloride. Carbon tetrachloride is introduced to serve both as a reactant and a diluent in the reaction zone in an amount sufficient to maintain the reaction temperature between about 500° and about 700° C. The carbon tetrachloride can be either in the vapor phase or liquid phase or a mixture of vapor and liquid phases.

The amounts of hydrogen and chlorine introduced into the reaction zone depend on the amount of carbon tetrachloride that is converted to perchloroethylene. The particular amounts are also a function of the reactor conditions, i.e. temperature, pressure, residence time. As more carbon tetrachloride is converted, more hydrogen is needed to supply the heat, however, less chlorine is required.

A gaseous product mixture containing unconverted carbon tetrachloride, chlorine, perchloroethylene and hydrogen chloride is withdrawn from the reaction zone and condensed, whereupon perchloroethylene, hydrogen chloride and any heavy ends are separated from the mixture. The process is characterized by a net consumption of carbon tetrachloride.

DESCRIPTION OF THE PREFERRED EMBODIMENTS OF THE INVENTION

The pyrolysis of carbon tetrachloride to form perchloroethylene is represented by the following equation:

$$2 CCl_4 + Heat \rightarrow C_2Cl_4 + 2 Cl_2 \qquad (1)$$

The reaction is an equilibrium reaction that is endothermic and favors the formation of carbon tetrachloride under conventional conditions. The promotion of the formation of perchloroethylene, a commercially important product, accompanied by maximum consumption of unwanted carbon tetrachloride is increasingly recognized as being desirable.

It has been found that the addition of elemental hydrogen and chlorine to the reactor can result in an increase in the amount of carbon tetrachloride consumed during production of perchloroethylene by pyrolysis while at the same time providing the heat required for the pyrolysis of the carbon tetrachloride. The elemental hydrogen reacts with a portion of the chlorine in the reactor, as shown in equation (2):

$$H_2 + Cl_2 \rightarrow 2\ HCl + Heat \qquad (2)$$

As this reaction generates heat in the reaction zone, if thus helps to drive forward the endothermic reaction of equation (1), which results in the production of perchloroethylene, without the need for external heating of the reactor as required by the prior art.

It has further been found, however, that this release of heat requires control and that this control can be achieved by having excess carbon tetrachloride in the reactor where it thus acts as a diluent. The result is that under fixed reaction zone conditions of temperature and pressure, and in the presence of hydrogen and chlorine, an increase in the conversion of carbon tetrachloride to perchloroethylene, as shown by equation (1), is obtained.

By combining reactions (1) and (2), this theoretically produces the overall net reaction shown below:

$$2\ CCl_4 + 2\ H_2 \rightarrow C_2Cl_4 + 4\ HCl \qquad (3)$$

In addition to consuming carbon tetrachloride, net reaction (3) produces perchloroethylene without any substantial or significant formation of undesirable heavy ends, such as hexachloroethane, hexachlorobutadiene and hexachlorobenzene. This is a further advantage of the process because of environmental difficulties and expense associated with the disposal of such heavy ends.

The present invention is directed to a process for the manufacture of perchloroethylene by the noncatalytic thermal pyrolysis of carbon tetrachloride in the presence of elemental hydrogen and chlorine at relatively low temperatures, for example between about 500° and about 700° C., and preferably between about 575° and about 625° C., wherein consumption of unwanted carbon tetrachloride is maximized while the production of heavy ends is minimized.

As stated earlier herein, the hydrogen and chlorine are introduced into the reaction zone in amounts sufficient to provide heat for the pyrolysis of carbon tetrachloride. The amount of hydrogen introduced will depend upon the reaction conditions as well as the amount of carbon tetrachloride and chlorine present in the reaction zone. In general, the mole ratio of hydrogen to carbon tetrachloride in the feed mixture is between about 0.1 and about 2.0, and preferably between about 0.3 and about 0.9. Chlorine is introduced into the reaction zone either as elemental chlorine or as a product of the pyrolysis reaction of carbon tetrachloride as shown in reaction (1). The chlorine is introduced in an amount at least sufficient to completely react with the hydrogen, as shown in reaction (2), to produce hydrogen chloride and to provide sufficient heat energy to convert carbon tetrachloride to perchloroethylene. In a preferred embodiment, chlorine is introduced in an amount sufficient to result in between about 0.1% and about 15.0%, more preferably between about 5.0% and about 8.5%, of free, i.e., unreacted, chlorine in the reactor effluent or product mixture, which is commonly described as excess chlorine. Excess chlorine in the reactor effluent or product mixture ensures that no unreacted hydrogen is present in the effluent and also prevents the formation of carbon. An additional benefit of excess chlorine being introduced into the reaction zone, as stated in U.S. Pat. Nos. 2,442,324 and 2,727,076, is a reduction in the formation of heavy ends.

The carbon tetrachloride is introduced into the reaction zone in an amount sufficient not only to serve as the principal reactant but also to maintain the temperature between about 500° and about 700° C., preferably between about 575° and about 625° C., by serving as a diluent in the reaction. Temperatures below about 500° C. result in lower conversions of carbon tetrachloride to perchloroethylene, while the higher temperatures of conventional pyrolysis reactions encourage side reactions and carbon formation. If desired, inert diluents such as hydrogen chloride and/or nitrogen may be used to help control reactor temperatures. However, it is preferred to recycle carbon tetrachloride from the process separation and/or distillation steps as well as introduce extraneous carbon tetrachloride diluent in order to control reactor temperatures. Recycling carbon tetrachloride increases perchloroethylene production while maximizing carbon tetrachloride consumption. Perchloroethylene may also be recycled, however, it is not preferred as the ability to minimize carbon tetrachloride is reduced. The specific amount of carbon tetrachloride added will depend upon whether the carbon tetrachloride is introduced in the vapor phase, the liquid phase or as a mixture of vapor and liquid phases, the proportions of hydrogen and chlorine present, and the temperature and pressure of the reaction zone.

The carbon tetrachloride may be introduced into the reaction zone either as a liquid or a vapor or a mixture of liquid and vapor, and it may be introduced either as a pure compound or as part of a mixed stream containing other chlorinated hydrocarbons such as chloroform, perchloroethylene, trichloroethylene, hexachlorobutadiene, hexachlorobenzene or hexachloroethane. However, it is preferred to use a chloro-organic stream which has a carbon tetrachloride concentration of at least 50 weight percent.

Figure 2:
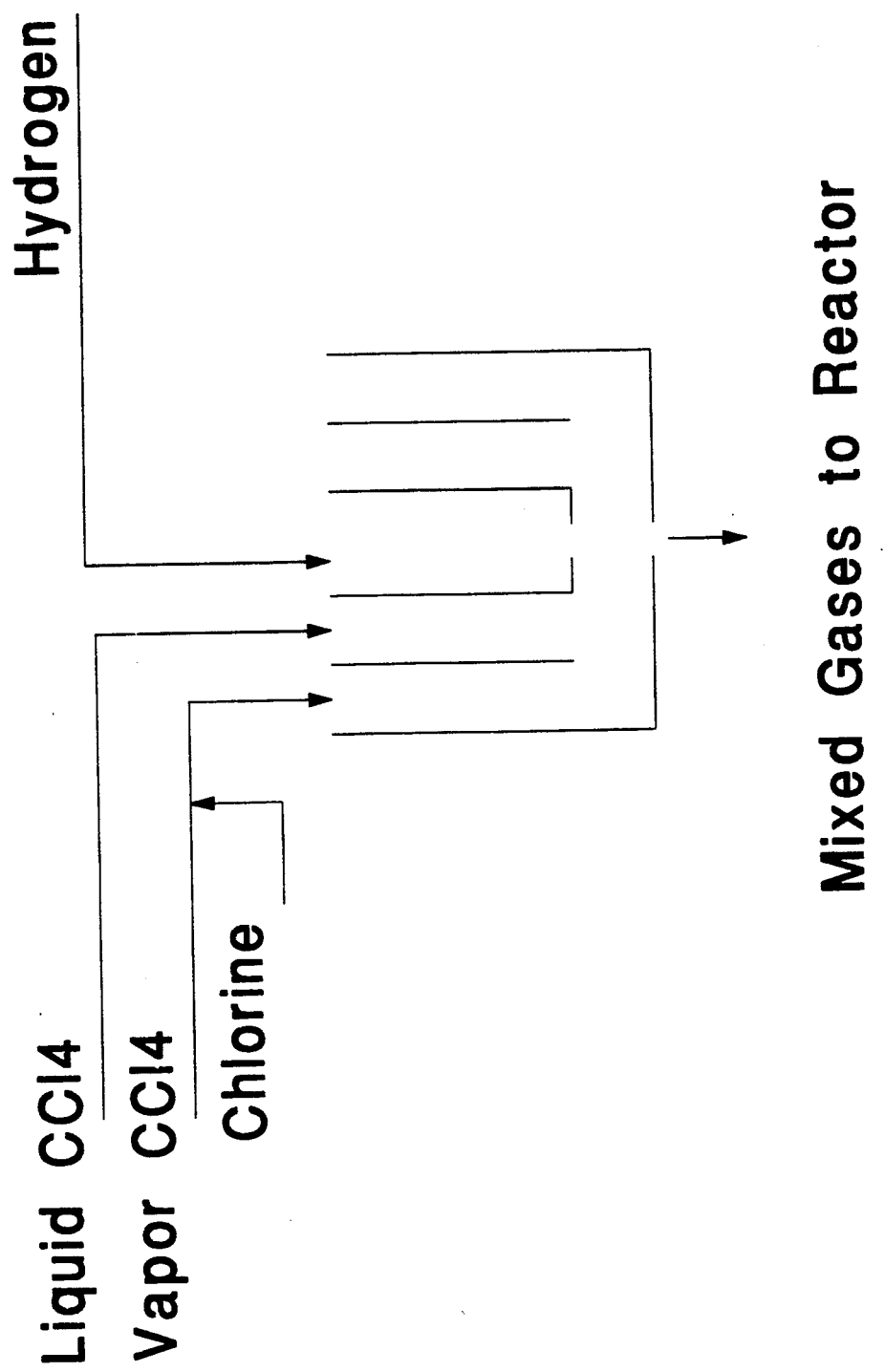

The reactants comprising the carbon tetrachloride, chlorine and hydrogen, including excess carbon tetrachloride which serves as a diluent, can be injected directly into the reaction zone without a mixing nozzle if all the reactants and diluent are in the vapor phase, as is common in the prior art. However, if the carbon tetrachloride is at least partially in the liquid phase, the carbon tetrachloride, chlorine and hydrogen are first introduced into an inlet of a mixing nozzle which is inserted or discharges into the reaction zone to achieve pre-mixing of the feed material. This practice improves the mixing efficiency of the reactants and thus increases the ability of the reaction zone to produce the desired products. Two types of mixing arrangements for introducing feed into the reaction zone through a mixing nozzle are schematically represented in FIGS. 1 and 2. These diagrams are meant only to be illustrative of the concept and should not be construed as all inclusive, thus limiting the invention.

As shown in FIG. 1, the liquid carbon tetrachloride, chlorine and hydrogen can be introduced into the mixing zone of the mixing nozzle inserted into the reactor to pre-mix the reactants. The reactor feed material enters the mixing zone and is inserted or discharges into the reaction zone of the reactor. The products of the reaction are then discharged from the reactor.

FIG. 2 illustrates the mixing diagram for feeding a mixture of liquid carbon tetrachloride and vapor carbon tetrachloride into the reactor. When a mixture of liquid and vapor carbon tetrachloride is fed into the reactor, it may be preferred in some cases for at least a portion of the vapor carbon tetrachloride and hydrogen to be fed into the reactor in a feed port separate from the mixing nozzle in which the chlorine and remaining liquid and/or vapor carbon tetrachloride are fed. The hydrogen is preferably fed with a portion of the vapor carbon tetrachloride in order to prevent carbon formation from hot spots, i.e., localized zones of high temperature in the reactor due to rapid reaction with insufficient cooling or mixing. Although not preferred, the chlorine may be fed into the reactor in a feed port separate from the mixing nozzle in which the carbon tetrachloride and hydrogen are fed.

While the process of the present invention has been described as being conducted in one reactor, the present invention alternatively can be carried out in two separate reactor stages operating in series. The first stage consists of reacting the carbon tetrachloride with chlorine and hydrogen in the presence of excess carbon tetrachloride diluent. The reactor effluent is fed to a second stage reactor wherein additional chlorine and/or hydrogen is injected.

Various factors are important in controlling the degree of mixing of the liquid diluent with the other reactants and diluent that are supplied in the vapor phase. These factors include the manner in which the liquid is introduced into the reaction zone of the reactor, the temperature and pressure of the liquid feed that is injected, the identity or composition of the liquid feed, the velocities of the materials to be mixed, and the conditions inside the reactor zone itself. In a preferred embodiment, the vapor feeds are introduced into the reaction zone of the reactor with a velocity through the orifice in the nozzle of at least about 30 meters per second (100 feet per second) and preferably between about 60 and about 77 meters per second (200 and 250 feet per second). The upper limit on the velocity is sonic velocity, although such high velocity is not preferred. Although not essential to the invention, it may be desirable to heat the liquid and/or vapor feeds prior to injecting them into the reactor in order to increase the turbulence in the mixing zone of the mixing nozzle. Heating the vapor feed to a higher temperature increases the volumetric flow of the gas, which increases the velocity at which the vapor feed is introduced into the reaction zone and results in better mixing of the gases. Heating the liquid feed to a higher temperature increases its viscosity, which makes the liquid easier to atomize and results in better dispersion of the liquid in the vapor feed. One skilled in the art of nozzle design will recognize that additional methods may be useful in obtaining a high degree of turbulence in the mixing zone to promote good mixing prior to entering the reaction zone.

Reactor pressure is important, but not critical. While the preferred operating pressure is between about 0 and about 4.5 atmospheres absolute (50 psig), higher pressures can be employed. The reactor can either be a back-mixed or plug flow type with suitable refractory lining as is common in the industry.

The perchloroethylene product may be purified by conventional methods illustrated in the prior art, such as effluent quenching, condensing, and distillation in order to separate the perchloroethylene product from unconverted carbon tetrachloride, hydrogen chloride, chlorine and other by-products.

The invention may be understood in more detail from the following examples. It should be understood that these examples are illustrative only and should not to be construed as limiting the invention which is set forth in the appended claims.

EXAMPLE 1

Vaporized chlorine, elemental hydrogen, and liquid carbon tetrachloride were continuously introduced into a back-mixed reactor chamber. The reactor chamber consisted of a carbon lined vessel consisting of about 1.9 cubic feet of volume. The reaction chamber was maintained at a temperature of approximately 595° C. and 3.7 atmospheres absolute pressure. The hot reaction gases at the exit of the reactor were indirectly cooled with water in a distillation-type quench tower with a bottoms temperature of about 165° C. The vapors of carbon tetrachloride and perchloroethylene going overhead of the quench tower were condensed by indirect cooling to separate them from the hydrogen chloride and unreacted chlorine, and fractionally distilled to recover the product. All of the carbon tetrachloride was fed as a liquid.

The results are shown in Table I.

EXAMPLE 2

Example 1 is repeated with the exception that the carbon tetrachloride was introduced as a mixture of vapor and liquid. The results are shown in Table I.

TABLE I

| Effect of Hydrogen Addition on Pyrolysis of $CCl_4$ | | |
|---|---|---|
| Example No. | 1 | 2 |
| Feeds, kg/hr | | |
| $Cl_2$ | 7.0 | 14.1 |
| Hydrogen | .206 | .363 |
| Liquid $CCl_4$ | 20.3 | 24.3 |
| Vapor $CCl_4$ | 0.0 | 41.0 |
| Total | 27.5 | 80.0 |
| Excess $Cl_2$, vol. % (in reactor effluent) | 5.7 | 8.0 |
| Molar Ratio of Reactants | | |
| $H_2/CCl_4$ | 0.77 | 0.42 |
| Products, kg/hr | | |
| $C_2Cl_4$ | 2.0 | 4.6 |
| $C_4Cl_6$ | .005 | 0.0 |
| $C_6Cl_6$ | 0.0 | .014 |
| HCl | 7.5 | 13.2 |
| $CCl_4$ Consumed, kg/hr | 3.7 | 8.6 |
| Wt. Ratio of $C_2Cl_4$ Produced to $CCl_4$ Consumed | | |
| $C_2Cl_4/CCl_4$ | .55 | .54 |
| Wt. Ratio of Products | | |
| Heavy ends/$C_2Cl_4$ | .002 | .003 |

As seen in Table I, the pyrolysis of carbon tetrachloride to perchloroethylene is maximized by the introduction of elemental hydrogen into the reaction zone while minimizing the production of unwanted heavy ends. The mole ratio of hydrogen to carbon tetrachloride added to the reactor is most preferably between about 0.4 and about 0.8.

With the present teaching in hand, persons skilled in the art will be able to determine the optimum mole ratio of hydrogen to carbon tetrachloride by performing routine preliminary tests for each case. The particular ratio, however, will depend upon, for example, the particular reactor conditions, the amount of chlorine introduced, and whether the carbon tetrachloride is in the vapor or liquid phase, or is a mixture of the vapor and liquid phases.

While the invention has been described in terms of certain preferred embodiments, modifications obvious to one with ordinary skill in the art may be made without departing from the scope of the present invention.

What is claimed is:

1. A noncatalytic thermal process for making perchloroethylene and hydrogen chloride from carbon tetrachloride, in the presence of hydrogen under conditions which maximize consumption of carbon tetrachloride, which process comprises introducing the following materials into a reaction zone:
   (a) carbon tetrachloride as the principal reactive compound;
   (b) elemental hydrogen and chlorine, the hydrogen and chlorine being introduced in amounts sufficient to provide heat for the pyrolysis of carbon tetrachloride at a reaction temperature between about 500° and about 700° C.; and
   (c) excess carbon tetrachloride as a diluent in an amount sufficient to maintain the reaction temperature between about 500° and about 700° C.;
   and withdrawing a product mixture from the reaction zone, condensing the product mixture, and separating perchloroethylene from the product mixture.

2. The process of claim 1, wherein the mole ratio of hydrogen to carbon tetrachloride added into the reaction zone is between about 0.1 and about 2.0.

3. The process of claim 2, wherein the mole ratio of hydrogen to carbon tetrachloride introduced into the reaction zone is between about 0.4 and about 0.8.

4. The process of claim 1, wherein the diluent comprising carbon tetrachloride is in the liquid phase.

5. The process of claim 1, wherein the diluent comprising carbon tetrachloride is in the vapor phase.

6. The process of claim 1, wherein the diluent comprising carbon tetrachloride is a mixture of liquid and vapor phase carbon tetrachloride.

7. The process of claim 6, wherein the elemental hydrogen, chlorine and mixture of liquid and vapor carbon tetrachloride are introduced into the reaction zone by means of a mixing nozzle.

8. The process of claim 7, wherein the reactants are pre-mixed in a mixing zone of the mixing nozzle.

9. The process of claim 6, wherein the hydrogen is fed with a portion of the vaporized carbon tetrachloride into the reaction zone through a feed port separate from the mixing nozzle through which the chlorine and remaining carbon tetrachloride are fed.

10. The process of claim 1, wherein the carbon tetrachloride separated from the product mixture is recycled to the reaction zone.

11. The process of claim 1, wherein chlorine introduced as elemental chlorine and chlorine generated in the reaction zone as a product of pyrolysis of carbon tetrachloride are present in the reaction zone in an amount sufficient to convert the hydrogen chloride, provide the heat for the pyrolysis of carbon tetrachloride and leave free chlorine in the resulting converted product mixture.

12. The process of claim 11, wherein the chlorine is introduced in an amount sufficient to leave between about 0.1 and about 15.0 volume percent of free chlorine in the resulting converted product mixture.

13. The process of claim 12, wherein the chlorine is introduced in an amount sufficient to leave between about 5.0 and about 8.5 volume percent of free chlorine in the resulting converted product mixture.

14. The process of claim 3, wherein the vapor feeds are introduced into the reaction zone with a velocity of at least about 30 meters per second.

15. The process of claim 14, wherein the vapor feeds are introduced into the reaction zone with a velocity of between about 60 and about 77 meters per second.

16. The process of claim 3, wherein the reaction temperature is between about 575° and 625° C.

17. The process of claim 16, wherein the pressure in the reaction zone is between about 0 and about 10 atmospheres.

18. The process of claim 17, wherein the pressure in the reaction zone is between about 1.0 and about 4.5 atmospheres absolute.

19. The process of claim 17, wherein said reaction zone is in a back-mixed reactor or a plug flow type.

* * * * *